United States Patent
Ohta et al.

(10) Patent No.: US 6,180,124 B1
(45) Date of Patent: Jan. 30, 2001

(54) COSMETIC COMPOSITION

(75) Inventors: Hiroshi Ohta; Kumiko Hosokawa; Junichi Fukasawa; Kenzo Koike; Masaki Shimizu, all of Tokyo (JP)

(73) Assignee: Kao Corporation, Tokyo (JP)

( * ) Notice: Under 35 U.S.C. 154(b), the term of this patent shall be extended for 0 days.

(21) Appl. No.: 09/340,012

(22) Filed: Jun. 28, 1999

(30) Foreign Application Priority Data

Jul. 21, 1998 (JP) .................................................. 10-205320
Jul. 21, 1998 (JP) .................................................. 10-205466

(51) Int. Cl.$^7$ ............................... A61K 6/00; A61K 9/14; A61K 9/50; A01N 25/24
(52) U.S. Cl. ......................... 424/401; 424/407; 424/489; 424/499; 424/502
(58) Field of Search .................................. 424/401, 407, 424/489, 494, 499

(56) References Cited

U.S. PATENT DOCUMENTS

| | | | |
|---|---|---|---|
| 4,159,316 | 6/1979 | Januszewski et al. | 424/49 |
| 5,480,632 * | 1/1996 | Orr et al. | 424/63 |
| 5,688,930 * | 11/1997 | Bertho et al. | 536/18.6 |
| 5,744,126 | 4/1998 | Horino et al. | 424/59 |

FOREIGN PATENT DOCUMENTS

| | | | |
|---|---|---|---|
| 0 612 516 | 8/1994 | (EP) . | |
| 0 897 719 | 2/1999 | (EP) . | |
| 1292352 * | 10/1972 | (GB) | 3/14 |
| 1357 000 | 6/1974 | (GB) . | |

* cited by examiner

Primary Examiner—Thurman K. Page
Assistant Examiner—S. Tran
(74) Attorney, Agent, or Firm—Oblon, Spivak, McClelland, Maier & Neustadt, P.C.

(57) ABSTRACT

The invention relates to a cosmetic composition comprising (A) a polyhydric alcohol and (B) a finely particulate metal oxide, wherein water is substantially not contained. The cosmetic composition has an optimum viscosity, undergoes no precipitation of particles, spreads well upon use and has good easiness of washing off and is hence particularly useful as a massaging cosmetic.

14 Claims, No Drawings

COSMETIC COMPOSITION

BACKGROUND OF THE INVENTION

1. Field of the Invention

The present invention relates to a cosmetic composition which gives users a warmed and pleasant feeling upon application thereof, has an excellent moisturizing effect, and is good in spreadability on and conformability to the skin and easy to be washed off.

2. Description of the Background Art

Non-aqueous cosmetic compositions comprising a polyhydric alcohol have moisturizing and warming effects and are hence utilized as massaging cosmetics and the like (Japanese Patent Application Laid-Open No. 320038/1993). It is also known to incorporate a thickening polymer soluble in a polyhydric alcohol, or silica gel in order to facilitate the application of the polyhydric alcohol to the skin (Japanese Patent Application Laid-Open Nos. 87158/1998, 194327/1998 and 87165/1998).

However, in order to thicken the resulting composition with the thickening polymer alone, it is necessary to use a great amount of the thickening polymer. In addition, the dependency of the viscosity of the composition on temperature becomes high, which has involved problems that the spreadability upon application to the skin at low temperatures becomes poor, that the flowability at high temperatures becomes too high to take the composition with fingers, and that when particles such as a scrubber are incorporated, the precipitation of the particles are observed at high temperatures. On the other hand, the system making use of the silica gel has involved such problems that the pH is low, and easiness of washing off becomes poor due to water-insoluble silica gel.

Accordingly, there has been a demand for development of a cosmetic composition which can make good use of the excellent properties of the polyhydric alcohol, and is good in spreadability on and conformability to the skin and easy to be washed off.

SUMMARY OF THE INVENTION

The present inventor has found that when a polyhydric alcohol and a finely particulate metal oxide are used in combination in such a manner that water is substantially not contained, a cosmetic composition, which can prevent its flowability from heightening at high temperatures, can be well taken with fingers, can also prevent precipitation of particles, has good thixotropic property, is easy to use, spreads well and has good easiness of washing off, can be provided with a moderate viscosity.

It has also been found that when exothermic powder is incorporated into the above composition, such a composition can give users a far excellent warmed feeling, that when a clay mineral is incorporated, the temperature stability of the composition is improved, and that when a polyhydric alcohol-soluble polymer is incorporated, the viscosity of the composition is optimized, and the precipitation of particles can be prevented more effectively.

According to the present invention, there is thus provided a cosmetic composition comprising (A) a polyhydric alcohol and (B) a finely particulate metal oxide, wherein water is substantially not contained.

According to the present invention, there are also provided cosmetic compositions comprising exothermic powder, a clay mineral and/or a polyhydric alcohol-soluble polymer in addition to the above components.

DETAILED DESCRIPTION OF THE PREFERRED EMBODIMENTS

Examples of (A) the polyhydric alcohol useful in the practice of the present invention include compounds having at least two hydroxyl groups in a saturated or unsaturated hydrocarbon skeleton which may have an ether bond. The hydrocarbon skeleton is preferably a linear, branched or cyclic alkyl or alkenyl group. Further, those which form a ring through an ether bond, such as saccharides, may also be included. Specific examples of the polyhydric alcohol include alkylene glycols such as ethylene glycol, propylene glycol, butylene glycol, amylene glycol and hexylene glycol; dialkylene glycols such as diethylene glycol, dipropylene glycol, diethylene glycol monomethyl ether and diethylene glycol monoethyl ether; glycerols such as glycerol, diglycerol, triglycerol and polyglycerols; sugar alcohols such as sorbitol; and polyethylene glycols and polypropylene glycols. Of these, propylene glycol, butylene glycol and polyethylene glycols (preferably, those having a molecular weight of 200 to 100,000, particularly 200 to 6,000) are particularly preferred from the viewpoints of a feeling upon use and moisturizability. The butylene glycol includes 1,3-butanediol and 3-methyl-1,3-butanediol.

These polyhydric alcohols may be used either singly or in any combination thereof and are incorporated in a proportion of 1 to 95% by weight (hereinafter indicated merely by "%") based on the total weight of the composition. They are preferably incorporated in a proportion of 5 to 90%, particularly 10 to 70% from the viewpoint of a feeling upon use.

The finely particulate metal oxide of the component (B) preferably has a specific surface area of 10 to 1,000 $m^2/g$, particularly 40 to 900 $m^2/g$ from the viewpoints of thickening effect and a feeling upon use. Further, the finely particulate metal oxide preferably has an average particle diameter (primary particle diameter) of 1 $\mu m$ or smaller, more preferably 2 to 100 nm, most preferably 5 to 30 nm from the viewpoints of a feeling upon use and stability. Specific examples thereof include aluminum oxide, titanium oxide, zinc oxide and iron oxide, with aluminum oxide and titanium oxide being particularly preferred.

The specific surface area is a value measured in accordance with the BET method making use of the absorption of nitrogen gas at the temperature of liquid nitrogen. The average primary particle diameter is a value determined by measuring diameters of 3,000 to 5,000 particles which have been photographed through an electron microscope, and arithmetically average the values obtained.

These finely particulate metal oxides may be used in any combination thereof and are incorporated in a proportion of 0.1 to 50% based on the total weight of the composition. When they are incorporated in a proportion of 0.5 to 30%, particularly 1 to 10%, a preferable thickening effect can be achieved.

A mixing ratio [(A):(B)] of the component (A) to the component (B) is preferably 100:1 to 2:1, particularly 40:1 to 3:1 by weight from the viewpoint of feeling upon use.

The cosmetic composition according to the present invention is a composition which does substantially not contain water. The term "substantially not contain water" as used herein does not mean excluding any composition in which a small amount of water is present, so far as the composition can generate sufficient heat of hydration when it comes into contact with external water. In the cosmetic composition according to the present invention, the content of water is at most about 5%.

When (C) exothermic powder is incorporated into the cosmetic composition according to the present invention, a stronger warmed feeling can be given users, and an effect as a massaging cosmetic is enhanced. It is preferred from the viewpoints of irritation to the skin and a feeling of roughness that the exothermic powder should be powder having an average particle diameter of 20 μm or smaller and substantially containing no particles having a particle diameter of 45 μm or greater. The term "substantially containing no particles having a particle diameter of 45 μm or greater" as used herein means that the amount of the particles having a particle diameter of 45 μm or greater is 2.0% or less, preferably 1.0% or less based on the total weight of the exothermic powder, and preferably that no such great particles are detected.

Non-aqueous cosmetic compositions comprising exothermic powder are described in U.S. Pat. No. 3,250,680, Japanese Patent Application Laid-Open No. 100411/1994 and Japanese Patent Application Laid-Open No. 336413/1994. However, the particle diameter of the exothermic powder incorporated into these cosmetic compositions is not limited in any way, and so such compositions are not preferred from the viewpoint of irritativeness to the skin.

The conditions of the particle diameter as to the exothermic powder are preferably satisfied at a stage of the raw material upon formulation of the cosmetic composition. However, particles having a particle diameter of 45 μm or greater may be removed by grinding, filtration and/or the like after the formulation to satisfy the conditions at the time the cosmetic composition is prepared. The particle diameter of the exothermic powder was measured by means of a laser diffraction/scattering type particle size distribution meter LA-910 (manufactured by Horiba Ltd.) using a batch cell and water as a solvent.

No particular limitation is imposed on the exothermic powder so far as it reacts with water to generate heat. Examples of the exothermic powder include those which can raise the temperature of water by at least 2° C., preferably at least 5° C. as the maximum reachable temperature when mixed with the equal weight of water at 25° C. More specifically, the maximum reachable temperature can be determined in the following manner.

[Testing Method 1]

Equal weights of water of 25° C.±1° C. and exothermic powder are mixed in a container such as a beaker under an atmosphere controlled at a fixed temperature within 25° C.±5° C. (temperature difference per hour: ±1° C.). When the mixture in the equal weights becomes a hard paste, and so successful mixing cannot be conducted, however, the mixing ratio of water to the exothermic powder may be optionally changed. The mixing ratio is determined by the dispersibility of the exothermic powder in water and may be preferably such that when water and the exothermic powder are mixed, they can be uniformly mixed with each other within 30 seconds. In this case, it is only necessary to calculate out the maximum reachable temperature upon mixing in equal weights from the quantity of exothermic heat at that time. After the uniform mixing, the temperature of the mixture is recorded after 5 seconds, 10 seconds and 30 seconds, and at intervals of 1 minute after that. The mixture is stirred by manual or mechanical shaking in vertical or lateral directions or by giving a turn, or by mechanical stirring using a magnetic stirrer, or a motor and an agitating blade. The stirring may be conducted either continuously or intermittently. The maximum temperature (° C.) measured within 1 hour from the beginning of the mixing is regarded as the maximum reachable temperature.

Examples of the exothermic powder exhibiting the above-described exothermic behavior include activated zeolites; sulfates such as magnesium sulfate, aluminum potassium sulfate and calcium sulfate; calcium chloride, sodium carbonate, metaphosphates, pyrophosphates, etc. Of these, the activated zeolites are preferred.

The activated zeolites are preferably activated zeolites such as zeolite A-3, zeolite A-4 and zeolite A-5 represented by the following formula:

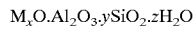

$$M_xO \cdot Al_2O_3 \cdot ySiO_2 \cdot zH_2O$$

wherein M is an alkali metal or alkaline earth metal, and x, y and z are independently an optional number. Zeolites subjected to a treatment such as ion exchange or neutralization may also be used.

Such a zeolite can be obtained by preparing, purifying, grinding, calcining and classifying in accordance with a method known per se in the art. A desired activated zeolite can be obtained by calcining and dehydrating a raw zeolite at about 300 to 600° C. and then storing it in dry air as described in, for example, EP Patent No. 187912 (Japanese Patent Application Laid-Open No. 204111/1986).

The exothermic powder is preferably incorporated in a proportion of 1 to 50%, particularly 5 to 40% based on the total weight of the cosmetic composition according to the present invention from the viewpoint of a warming effect by exothermic heat and a moisturizing effect.

When (D) a clay mineral is incorporated into the cosmetic composition according to the present invention, the temperature stability of the viscosity of the composition can be improved. No particular limitation is imposed on the clay mineral so far as it is that commonly used in the classical cosmetic compositions. Examples thereof include kaolin, bentonite, smectite, talc, mica, etc. Of these, kaolin is particularly preferred.

These clay minerals may be used either singly or in any combination and are preferably incorporated in a proportion of 5 to 60%, particularly 5 to 30% based on the total weight of the composition in that an optimum viscosity and good temperature stability can be imparted.

Further, (E) a polyhydric alcohol-soluble polymer may be incorporated into the cosmetic composition according to the present invention. This polymer has effects of controlling the viscosity of the system and preventing precipitation of powder. Examples of such a polymer include cellulosic polymers such as hydroxypropyl cellulose, hydroxymethylpropyl cellulose, acrylic acid-alkyl methacrylate copolymers, etc., with hydroxypropyl cellulose and hydroxymethylpropyl cellulose being particularly preferred.

The above-mentioned polymers may be used either singly or in any combination thereof and are preferably incorporated in a proportion of 0.01 to 10%, more preferably 0.01 to 5%, most preferably 0.05 to 1% from the viewpoint of a feeling upon use.

In the cosmetic compositions according to the present invention, various ingredients commonly used in the classical cosmetic compositions, for example, surfactants, oily substances, lubricants, wetting agents, antiseptics, germicides, antiphlogistics, astringents, hemostatics, analgesics, vitamins and derivatives thereof, chelating agents, foaming agents, refrigerants, cold sensation-imparting agents, rust preventives for metals, animal and plant extracts, colorants, antioxidants, perfume bases, etc., may be suitably incorporated in addition to the above-described components so far as no detrimental influence is thereby imposed on the effects of the present invention.

The cosmetic compositions according to the present invention are preferably kept at a viscosity of 10 to 1,000 Pa·s, particularly 20 to 200 Pa·s. The viscosity is measured under rotation for 60 seconds at 5 rpm by means of a Brookfield viscometer, Rotor T-D manufactured by Toki Sangyo K.K.

The cosmetic compositions according to the present invention can be prepared by mixing the above-described components in accordance with a method known per se in the art and are preferably used as massaging compositions and packs. In order to use the composition as a massaging composition, a part to be massaged, for example, a face, is wetted to apply the composition thereto, the face is massaged, and the composition is then washed off. In order to use it as a pack, for example, a face is wetted to apply the pack thereto, the face is held for a proper period of time in that state, and the pack is then washed off.

When the cosmetic composition according to the present invention is applied to the skin wetted with water, it is preferred that the temperature of the skin surface be raised by at least 2° C. from that before the application, or rise in temperature by at least 1° C. from that before the application is retained for at least 30 seconds. In the present invention, the measurement of the temperature of the skin surface when applied to the skin wetted with water is conducted in the following manner.

[Testing Method 2] Method for determining a change in the temperature of the skin:

After the skin (lower inner arm) of a panelist stayed for at least 1 hour under an atmosphere controlled at a fixed temperature of 20 to 30° C. (temperature difference per hour: ±1° C.) (hereinafter referred to as "room temperature") is wetted with a proper amount of water (room temperature ±1° C.), the temperature of the surface is measured by a non-contact thermometer (for example, CT-30 manufactured by K.K. Kosu) or thermograph to use this temperature as a reference value. A test sample (room temperature ±1° C.) is applied in an amount of 1 to 5 g (10 to 100 $cm^2$) to the skin wetted with water in the same manner as described above by fingers or a palm of the panelist. The temperature of the skin surface at the applied part is recorded at intervals of 1 second to 1 minute from the time the sample has been applied. A difference between the maximum temperature (° C.) for 10 minutes from the beginning of the measurement and the reference value is regarded as a rise in temperature. The time during which the rise in temperature is at least 1° C. is regarded at the exothermic time. When the panelist does not feel warm, such a sample is regarded as generating no exothermic heat.

EXAMPLES

Cosmetic compositions according to the present invention and comparative cosmetic compositions were obtained in accordance with the following respective formulations.

| Example 1: (Massaging cosmetic, viscosity at 25° C.: 68 Pa · s) | |
| --- | --- |
| Polyethylene glycol (average molecular weight: 400) | 50% |
| 1,3-Butanediol | 42.5% |
| Finely particulate aluminum oxide (specific surface area: 100 $m^2$/g, average particle diameter: 13 nm) | 7% |
| Hydroxypropyl cellulose | 0.5%. |
| Example 2: (Pack cosmetic, viscosity at 25° C.: 156 Pa · s) | |
| Polyethylene glycol (average molecular weight: 2,000) | 7% |
| Polyethylene glycol (average molecular weight: 400) | 30% |
| 3-Methyl-1,3-butanediol | 45% |
| Finely particulate aluminum oxide (specific surface area: 100 $m^2$/g, average particle diameter: 13 nm) | 3% |
| Kaolin | 15%. |
| Example 3: (Massaging cosmetic, viscosity at 25° C.: 30 Pa · s) | |
| Polyethylene glycol (average molecular weight: 400) | 30% |
| Propylene glycol | 59.5% |
| Finely particulate titanium oxide (specific surface area: 50 $m^2$/g, average particle diameter: 21 nm) | 10% |
| Hydroxymethyl cellulose | 0.5%. |
| Example 4: (Massaging cosmetic, viscosity at 25° C.: 68 Pa · s) | |
| Polyethylene glycol (average molecular weight: 400) | 50% |
| 1,3-Butanediol | 17.5% |
| Finely particulate aluminum oxide (specific surface area: 100 $m^2$/g, average particle diameter: 13 nm) | 7% |
| Hydroxypropyl cellulose | 0.5% |
| Activated zeolite (product of Tosoh Corp.; average particle diameter: 4 μm, substantially containing no particles having a particle diameter of 45 μm or greater) | 25%. |
| Comparative Example 1: (viscosity at 25° C.: 5 Pa · s) | |
| Polyethylene glycol (average molecular weight: 200) | 10% |
| Polyethylene glycol (average molecular weight: 400) | 30% |
| 1,3-Butanediol | 30% |
| Kaolin | 30%. |
| Comparative Example 2: (viscosity at 25° C.: 28 Pa · s) | |
| Polyethylene glycol (average molecular weight: 400) | 30% |
| Glycerol | 57% |
| Polyethylene glycol monolaurate | 3% |
| Silica gel (specific surface area: 15 $m^2$/g, average particle diameter: 4.0 μm) | 10%. |

Test Example 1

Each of the cosmetic compositions obtained above was used to evaluate it as to spreadability, easiness of massaging and easiness of washing off. Further, whether the cosmetic compositions underwent separation after stored at 25° C. for 1 week was visually observed.

(Evaluation method)

Each of the massaging cosmetics and pack cosmetic according to the present invention and the comparative compositions was applied to faces of 3 expert panelists to organoleptically evaluate it as to spreadability, easiness of massaging and easiness of washing off.

(Evaluation standard)

The spreadability, easiness of massaging and easiness of washing off were all evaluated in accordance with the following standard:

○: Two or three panelists judged to be good;

Δ: One panelist judged to be good;

×: No panelist judged to be good.

As a result, as shown in Table 1, the cosmetic compositions according to the present invention were far excellent in all the spreadability, easiness of massaging, easiness of washing off and occurrence of separation compared with the comparative compositions.

TABLE 1

|  | Example | | | Comp. Example | |
| --- | --- | --- | --- | --- | --- |
|  | 1 | 2 | 3 | 1 | 2 |
| Spreadability | ○ | ○ | ○ | X | Δ |
| Easiness of massaging | ○ | ○ | ○ | X | Δ |
| Easiness of washing off | ○ | ○ | ○ | X | Δ |
| Occurrence of separation (25° C., 1 week) | Not occurred | Not occurred | Not occurred | Occurred | Occurred |

Test Example 2

Cosmetic compositions according to Examples 1 and 4 were used. Each of the massaging cosmetics was applied to the healthy lower inner arm (n=5) to massage it for 10 seconds. The moisturizing effect after 30 seconds from the massage was evaluated by measuring a skin conductance value of the applied part by a SKICON 200 (manufactured by IBS K.K). As a result, as shown in Table 2, the cosmetic compositions according to the present invention were far excellent in moisturizing effect compared with water washing. A greater conductance value in Table 2 indicates a higher water content in the horny layer, i.e., a more improved moisturizing effect.

TABLE 2

|  | Skin conductance (μS) |
| --- | --- |
| Water washing | 75 |
| Example 1 | 100 |
| Example 4 | 120 |

Examples 5 and 6, and Comparative Examples 3 and 4

Massaging cosmetics having their corresponding compositions shown in Table 3 were prepared to measure viscosities thereof at 25° C. and 50° C. and moreover evaluate them as to stability (whether separation occurred after stored at 25° C. for 1 week or not) and spreadability on and conformability to the skin when applied to the skin. The results are shown collectively in Table 3.
(Evaluating method of spreadability on and conformability to the skin when applied to the skin)

Each of the massaging cosmetics was applied to 3 expert panelists to organoleptically evaluate it as to the spreadability on and conformability to the skin in accordance with the following standard:

⊚: Three panelists judged to be good;

○: One or two panelist judged to be good;

×: No panelist judged to be good.

TABLE 3

| | | | | (%) |
| --- | --- | --- | --- | --- |
| | Example | | Comp. Example | |
| Component | 5 | 6 | 3 | 4 |
| Polyethylene glycol molecular weight: 200) | 10.0 | — | — | 10.0 |

TABLE 3-continued

| | | | | (%) |
| --- | --- | --- | --- | --- |
| | Example | | Comp. Example | |
| Component | 5 | 6 | 3 | 4 |
| Polyethylene glycol molecular weight: 400) | 30.0 | 30.0 | 40.0 | 30.0 |
| Glycerol | 5.0 | 5.0 | 5.0 | — |
| 1,3-Butanediol | 15.0 | 28.7 | 33.5 | — |
| 3-Methyl-1,3-butanediol | — | — | — | 49.7 |
| Kaolin[1] | 20.0 | 13.0 | — | — |
| Finely particulate aluminum[2] oxide | 5.0 | 3.0 | — | — |
| Hydroxypropyl cellulose | — | 0.3 | 1.5 | 0.3 |
| Activated zeolite[3] | 15.0 | 20.0 | 20.0 | 10.0 |
| Viscosity (Pa · s) 25° C. | 70 | 60 | 20 | 1 |
| 50° C. | 65 | 58 | 5 | 0.6 |
| Occurrence of separation (25° C., 1 week) | Not occurred | Not occurred | Occurred | Occurred |
| Spreadability and conformability upon application | ⊚ | ⊚ | X | X |

[1]Average particle diameter: 4.5 μm.
[2]Specific surface area: 100 m²/g, average particle diameter: 13 nm.
[3]Average particle diameter: 4 μm; substantially containing no particles having a particle diameter, of 45 μm or greater.

Example 7

(Massaging cosmetic)

A cosmetic composition having the following formulation was prepared.

| | |
| --- | --- |
| Activated zeolite (average particle diameter: 4 μm; substantially containing no particles having a particle diameter of 45 μm or greater) | 20% |
| Polyethylene glycol 400 | 30% |
| 1,3-Butanediol | 34.5% |
| Finely particulate aluminum oxide (specific surface area: 100 m²/g, average particle diameter: 13 nm; detected no particles having a particle diameter of 45 μm or greater) | 7% |
| Kaolin (average particle diameter: 4.5 μm; substantially containing no particles having a particle diameter of 45 μm or greater) | 8% |
| Hydroxypropyl cellulose | 0.5%. |

(1) Quantity of exothermic heat of activated zeolite:
10 g of water was mixed with 10 g of the activated zeolite in accordance with Testing Method 1 to measure the maximum reachable temperature by a thermometer.
Maximum reachable temperature: 49° C.
(2) Quantity of exothermic heat of massaging cosmetic:
10 g of water of 25° C. was mixed with 10 g of the massaging cosmetic in a beaker to measure the maximum reachable temperature by a thermometer.
Maximum reachable temperature: 39° C.
(3) Measurement of particle diameter of activated zeolite:
The particle diameter of the activated zeolite was measured by means of a laser diffraction/scattering type particle size distribution meter LA-910 manufactured by Horiba Ltd. using a batch cell and water as a solvent.
(4) Particle diameter of massaging cosmetic:
The particle diameter of the massaging cosmetic was measured in the same manner as in the activated zeolite. As a result, no particle having a particle diameter of 45 μm or greater was observed.

| Example 8: (Massaging cosmetic) | |
|---|---|
| Polyethylene glycol 400 | 30% |
| 1,3-Butanediol | 20% |
| Glycerol | 2.5% |
| Sphingosine derivative | 0.5% |
| Liquid paraffin | |
| Activated zeolite (average particle diameter: 4 μm; substantially containing no particles having a particle diameter of 45 μm or greater) | 30% |
| Finely particulate aluminum oxide (specific surface area: 100 m$^2$/g, average particle diameter: 13 nm; substantially containing no particles having a particle diameter of 45 μm or greater) | 5% |
| Acrylic acid-methacrylic acid copolymer (PEMULEN TR-1, product of BF Goodrich Co.) | 1% |
| Spherical polyethylene beads (average particle diameter: 180 μm) | 3%. |

(1) Quantity of exothermic heat of activated zeolite:
The maximum reachable temperature was measured in accordance with Testing Method 1.
Maximum reachable temperature: 49° C.
(2) Quantity of exothermic heat of massaging cosmetic:
Ten grams of water of 25° C. was mixed with 10 g of the massaging cosmetic in a beaker to measure the maximum reachable temperature by a thermometer.
Maximum reachable temperature: 42° C.

| Comparative Example 5: | |
|---|---|
| Activated zeolite (average particle diameter: 22 μm; maximum particle diameter: 100 μm; containing 25% of particles having a particle diameter of 45 μm or greater) | 10% |
| Polyethylene glycol 400 | 30% |
| 1,3-Butanediol | 41% |
| Finely particulate aluminum oxide (specific surface area: 100 m$^2$/g, average particle diameter: 13 nm; maximum particle diameter: 45 μm) | 3% |
| Kaolin (average particle diameter: 4.5 μm; maximum particle diameter: 20 μm) | 15% |
| 4.5 μm; maximum particle diameter: 20 μm) | |
| Hydroxypropyl cellulose | 1.0%. |

The particle diameter of the powdery component in the resultant cosmetic composition was measured. As a result, 9% of particles were observed having a particle diameter of 45 μm or greater.

Test Example 3

The cosmetic compositions according to Examples 7 and 8 and Comparative Example 5 were used to evaluate them as to a feeling of roughness, an irritated feeling to the skin and a feeling of physical disorder when entered eyes.
(Evaluation method)
Each of the massaging cosmetics according to the present invention and the comparative composition was applied to faces of 3 expert panelists to organoleptically evaluate it as to a feeling of roughness, an irritated feeling to the skin and a feeling of physical disorder when entered eyes.
(Evaluation standard)
The feeling of roughness, irritated feeling to the skin and feeling of physical disorder when entered eyes were evaluated in accordance with the following standard:
○: Three panelists replied that they felt nothing;
Δ: One or two panelists replied that they felt nothing;
×: Three panelists replied that they felt.

As a result, as shown in Table 4, the cosmetic compositions according to the present invention gave users none of the feeling of roughness, irritated feeling to the skin and feeling of physical disorder when entered eyes. To the contrary, the comparative composition comprising the powder whose particle diameter conditions were outside the range according to the present invention gave users the feeling of roughness, irritated feeling to the skin and feeling of physical disorder when entered eyes.

TABLE 4

| | Feeling of roughness | Irritated feeling | Feeling of physical disorder when entered eyes |
|---|---|---|---|
| Example 7 | ○ | ○ | ○ |
| Example 8 | ○ | ○ | ○ |
| Comp. Ex. 5 | X | X | X |

This application is based on Japanese patent applications 10-205466 and 10-205320, both filed Jul. 21, 1998, the entire contents of which are hereby incorporated by reference.

What is claimed is:

1. A cosmetic composition comprising (A) a polyhydric alcohol and (B) a finely particulate metal oxide which has a specific surface area of 10 to 1,000 m$^2$/g and an average particle diameter of 1 μm or smaller, wherein a mixing ratio of (A):(B) is 100:1 to 2:1 by weight, and wherein water is substantially not contained.

2. The cosmetic composition according to claim 1, wherein (B) the finely particulate metal oxide is aluminum oxide or titanium oxide.

3. The cosmetic composition according to claim 1, which further comprises (C) exothermic powder.

4. The cosmetic composition according to claim 3, wherein (C) the exothermic powder is powder having an average particle diameter of 20 μm or smaller and substantially containing no particles having a particle diameter of 45 μm or greater.

5. The cosmetic composition according to claim 4, wherein (C) the exothermic powder is activated zeolite.

6. The cosmetic composition according to claim 1 or 3, which further comprises (D) a clay mineral.

7. The cosmetic composition according to claim 6, wherein (D) the clay mineral is kaolin.

8. The cosmetic composition according to claim 1 or 3, which further comprises (E) a polyhydric alcohol-soluble polymer.

9. The cosmetic composition according to claim 6, which further comprises (E) a polyhydric alcohol-soluble polymer.

10. A cosmetic composition comprising:
(A) a polyhydric alcohol;
(B) a finely particulate metal oxide which has a specific surface area of 10 to 1,000 m$^2$/g and an average particle diameter of 2 to 100 nm, and
(C) an exothermic powder having an average particle diameter of 20 μm or smaller and substantially containing no particles having a particle diameter of 45 μm or greater, wherein a mixing ratio of (A):(B) is 100:1 to 2:1 by weight, and
wherein water is substantially not contained.

11. The cosmetic composition of claim 1, wherein said finely particulate metal oxide has an average particle diameter of 2 to 100 nm.

12. A method of massaging comprising:

i) applying a cosmetic composition to a part to be massaged;

ii) massaging said area; and iii) washing off said composition, wherein said cosmetic composition comprises (A) a polyhydric alcohol and (B) a finely particulate metal oxide, wherein a mixing ratio of (A):(B) is 100:1 to 2:1 by weight, and wherein water is substantially not contained.

13. A method of packing comprising:

i) applying a cosmetic composition to a part to be packed; and ii) washing off said composition, wherein said cosmetic composition comprises (A) a polyhydric alcohol and (B) a finely particulate metal oxide, wherein a mixing ratio of (A):(B) is 100:1 to 2:1 by weight, and wherein water is substantially not contained.

14. A massaging composition or pack which comprises the cosmetic composition of claim 1.

* * * * *